(12) United States Patent
Brod

(10) Patent No.: US 9,175,058 B2
(45) Date of Patent: Nov. 3, 2015

(54) SOLUBLE IMMUNE RESPONSE SUPPRESSOR POLYPEPTIDES AND TREATMENT OF MULTIPLE SCLEROSIS AND OTHER AUTOIMMUNE DISEASES

(75) Inventor: Staley A. Brod, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 2642 days.

(21) Appl. No.: 11/570,221

(22) PCT Filed: Jun. 9, 2005

(86) PCT No.: PCT/US2005/020265
§ 371 (c)(1),
(2), (4) Date: Apr. 27, 2007

(87) PCT Pub. No.: WO2005/123107
PCT Pub. Date: Dec. 29, 2005

(65) Prior Publication Data
US 2007/0185030 A1 Aug. 9, 2007

Related U.S. Application Data

(60) Provisional application No. 60/578,232, filed on Jun. 9, 2004.

(51) Int. Cl.
*C07K 14/52* (2006.01)
*A61K 38/17* (2006.01)

(52) U.S. Cl.
CPC ............... *C07K 14/52* (2013.01); *A61K 38/17* (2013.01)

(58) Field of Classification Search
None
See application file for complete search history.

(56) References Cited

U.S. PATENT DOCUMENTS

| | | | |
|---|---|---|---|
| 5,973,122 A | 10/1999 | Chang | 530/380 |
| 2003/0004185 A1* | 1/2003 | Baroudy et al. | 514/316 |

FOREIGN PATENT DOCUMENTS

WO    WO 87/02677    5/1987

OTHER PUBLICATIONS

Martin, D., and Near, S.L. J. Neuroimmunol. 1995;61:241-245.*
Krakauer, R.S., et al. Science. 1977;196:56-59.*
Shoenfeld, Y., et al. Immunol. Letts. 1993;36:109-116.*
Zimecki, M. et al. Arch. Immunol. Therap. Exp. 1991;39:213-226.*
Aune and Pierce, "Activation of a suppressor T-cell pathway by interferon," *Proc. Natl. Acad. Sci. USA*, 79:3808-3812, 1982.
Aune and Pierce, "Preparation of soluble immune response suppressor and macrophage-derived suppressor factor," *J. Immunol. Methods*, 53:1-14, 1982.
Aune et al., "Production of the lymphokine soluble immune response suppressor (SIRS) during chronic experimental schistosomiasis mansoni," *J. Immunol.*, 135:2768-2771, 1985.
Aune and Pierce, "Mechanism of action of macrophage-derived suppressor factor produced by soluble immune response suppressor-treated macrophages," *J. Immunol.*, 127:368-372, 1981.
Aune, "Inhibition of soluble immune response suppressor activity by growth factors," *Proc. Natl. Acad. Sci. USA*, 82:6260-6264, 1985.
Aune, "Role and function of antigen nonspecific suppressor factors," *Crit. Rev. Immunol.*, 7:93-130, 1987.
Beck et al., "Increased Production of $IFN_{-g}$ and TNF precedes clinical manifestations in MS: Do cytokines trigger off exacerbations?" *Acta Neurol. Scand.*, 78:318-323, 1988.
Chofflon et al., "$TNF_{-\alpha}$ production as a possible predictor of relaphse in patients with MS," *Eur. Cytokine Netw.*, 3:523-531, 1992.
Dettke et al., "Correlation between interferon production and clinical disease activity in patients with multiple sclerosis," *J. Clin. Immunol.*, 17:293-300, 1997.
Devens and Webb, "Phenotypic identification of specific and nonspecific suppressor T-cell populations involved in the in vivo response to alloantigen," *Cell Immunol.*, 161:1-7, 1995.
Devens et al., "Antipeptide antibody specific for the N-terminal of soluble immune response suppressor neutralizes concanavalin A and IFN-induced suppressor cell activity in an in vitro cytotoxic T lymphocyte response," *J Immunol.*, 141(9):3148-3155, 1988.
Ibrahim et al., "Gene expression profiling of the nervous system in murine experimental autoimmune encephalomyelitis," *Brain*, 124:1927-1938, 2001.
Jones et al., "Encephalitogenic T lymphocytes develop from SJL/J hematopoietic cells transplanted into severe combined immunodeficient (SCID) mice," *J. Neuroimmunol.*, 57:155-164, 1995.
Krakauer et al., "Prevention of antoimmunity in experimental lupus erythematosus by soluble immune response suppressor," *Science*, 196:56-59, 1977.
Schnaper et al., "Identification and Initial Characterization of Concanavalin A- and Interferon-induced Human Suppressor Factors: Evidence for a Human Equivalent of Murine Soluble Immune Response Suppressor (SIRS)," *J. Immunol.*, 132:2429-2435, 1984.
Schnaper and Aune, "Identification of the lymphokine soluble immune response suppressor in urine of nephrotic children," *J. Clin, Invest.*, 76:341-349, 1985.
Schnaper and Aune, "Suppression of immune responses to sheep erythrocytes by the lymphokine soluble immune response suppressor (SIRS) in vivo," *J. Immunol.*, 137:863-867, 1986.
Schnaper et al., "Suppressor T cell activation by human leukocyte interferon," *J. Immunol.*, 131:2301, 1983.
Schnaper, "Divalent metal requirement for soluble immune response suppressor (SIRS) activity," Cell Immunol., 118(1):157-165, 1989.
Tadakuma et al., "Biological Expressions of Lymphocyte Activation. V. Characterization of a Soluble Immune Response Suppressor (SIRS) Produced by Concanavalin A-Activated Spleen Cells," J. Immunol., 117:323-330, 1976.

(Continued)

*Primary Examiner* — Gerald R Ewoldt
(74) *Attorney, Agent, or Firm* — Parker Highlander PLLC

(57) ABSTRACT

The present invention provides methods of treating multiple sclerosis, type 1 diabetes mellitus and other autoimmune diseases by administering a soluble immune response suppressor (SIRS) peptide or a variant thereof to an individual having such disease. The SIRS peptide or variant reduces the severity of or frequency of relapse of multiple sclerosis and reduces the inflammation associated with multiple sclerosis and other autoimmune diseases.

48 Claims, 7 Drawing Sheets

(56) References Cited

OTHER PUBLICATIONS

Tadakuma and Pierce, "Site of Action of a Soluble Immune Response Suppressor (SIRS) Produced by Concanavalin A-Activated Spleen Cell," *J. Immunol.*, 117:967-972, 1976.

Terajima, et al., "Cytokine Effects on the Down Regulation of Cytolytic T Cell Responses in Vitro," *Lymphokine Research*, 9:499-506, 1990.

Warrington, "Interaction of a lymphokine with normal human macrophages results in release of a suppressor factor for mitogen-induced immunoglobulin synthesis," *Scand. J. Immunol.*, 25:399-406, 1987.

Webb et al., "Putative N-terminal sequence of murine soluble immune response suppressor (SIRS): Significant homology with short neurotoxin 1," *Int. Immunol.*, 2:765-774, 1990.

Webb et al., "Purification and analysis of isoforms of soluble immune response suppressor (SIRS)," *J. Immunol.*, 135:3238-3242, 1985.

Zimecki et al., "Inhibition of interleukin 1 (IL-1)-elicited leukocytosis and LPS-induced fever by soluble immune response suppressor (SIRS)," *Immunopharmacology*, 19:39-46, 1990.

* cited by examiner

SOLUBLE IMMUNE RESPONSE SUPPRESSOR POLYPEPTIDES AND TREATMENT OF MULTIPLE SCLEROSIS AND OTHER AUTOIMMUNE DISEASES

CROSS-REFERENCE TO RELATED APPLICATIONS

This application is a national phase application under 35 U.S.C. §371 of International Application No. PCT/US2005/020265 filed Jun. 9, 2005 which claims priority to U.S. Provisional Application Ser. No. 60/578,232 filed Jun. 9, 2004, the entire text and figures of which disclosures are incorporated herein by reference without disclaimer.

BACKGROUND OF THE INVENTION

1. Field of the Invention

The present invention relates generally to the field of immunology. More specifically, the present invention relates to the uses of soluble immune response suppressor (SIRS) in the treatment of multiple sclerosis or other autoimmune diseases.

2. Description of the Related Art

Supernatant fluids from murine spleen cell cultures incubated with concanavalin A for 48 hours contain a factor, soluble immune response suppressor (SIRS), which suppressed plaque-forming cell responses to sheep erythrocytes in vitro (Tadakuma et al., 1976). Soluble immune response suppressor is non-dialyzable destroyed by high temperatures, pH 2, trypsin, chymotrypsin and absorbed by spleen and thymus which is suggestive of a glycoprotein. Supernatant fluids with the soluble immune response suppressor activity contained macrophage migration inhibitory factor (MIF). The cellular site of action of the soluble immune response suppressor appeared to be the macrophage (Tadakuma et al., 1976; Aune et al., 1981). Exposure of splenic or peritoneal exudate macrophages to soluble immune response suppressor suppressed antibody responses by untreated splenic lymphoid cells, whereas exposure of splenic lymphoid cells to soluble immune response suppressor was without effect.

Animal modeling using the soluble immune response suppressor also showed anti-autoimmune effects. Young NZB/W mice treated with injections of soluble immune response suppressor of supernatant from mouse spleen cells exposed to concanavalin A showed decreased immunoglobin levels, less antibody to cell nuclei, less proteinuria and less renal pathology as compared with NZB/W mice receiving a control preparation. Soluble immune response suppressor administration beginning at an early age appears to be an effective therapy of the autoimmune disorder in NZB/W mice (Krakauer et al., 1977).

A comparable soluble immune response suppressor system also appears to function in humans. Human polyclonal plaque-forming cell responses by concanavalin A, leukocyte interferon or by suppressor cells activated by these agents is preventable by levamisole, ascorbic acid, catalase, or 2-mercaptoethanol, agents known to interfere with murine soluble immune response suppressor activity. Furthermore, concanavalin A, immune interferon, and leukocyte interferon induced T lymphocytes releases proteins which suppressed immune responses.

Peripheral blood mononuclear cells and OKT8 positive T suppressor cells incubated with human IFN-α decreased pokeweed mitogen-stimulated polyclonal immunoglobin production and inhibited proliferation in mixed lymphocyte cultures. Suppression mediated by these cells was prevented by catalase, ascorbic acid, and 2-mercaptoethanol. These results suggest that IFN-α activated suppressor T cells in human peripheral blood mononuclear cell cultures have certain similarities to IFN-β or to concanavalin A-activated murine suppressor T cells (Schnaper et al., 1983). The similarities between these human suppressor factors and murine soluble immune response suppressor show the existence of a human soluble immune response suppressor pathway. (Schnaper et al., 1984)

Soluble immune response suppressor appears to be a generalized immunomodulatory molecule. IL-1-induced leukocytosis was inhibited or blocked in a dose-dependent manner by soluble immune response suppressor when administered intravenously to CBA mice. An antipyric activity of soluble immune response suppressor was observed in rabbits injected intravenously with lipopolysaccharide (LPS) (Zimecki et al., 1990). Soluble immune response suppressor given intravenously in one or two doses markedly reduced LPS-induced fever. Soluble immune response suppressor is a selective inhibitor of IL-1 activity with respect to T and B cells, rendering them unresponsive to IL-1 activation and/or maturation signals without reversing inhibition of autologous rosette formation induced by factors such as IL-4.

Chronic schistosomiasis mansoni is a helminthic infection characterized by cell-mediated anti-egg granulomatous reactions and a variety of associated immunoregulatory phenomena. There is a strong association between the presence of the soluble immune response suppressor in the serum, the production of the soluble immune response suppressor by intact lesions, and the chronic, immunomodulated stage of schistosomiasis mansoni. The presence of urinary soluble immune response suppressor suggest a possible role for soluble immune response suppressor in the suppressed immune responses often found in nephrotic syndrome with a striking correlation between detection of soluble immune response suppressor and the presence of steroid-responsive nephrotic syndrome.

Delayed Type Hypersensitivity (DTH) responses to footpad injection of sheep red blood cells (SRBC) also was inhibited by soluble immune response suppressor. The action of putative regulatory cells to mixed lymphocyte cultures was blocked by antiserum to the N-terminal sequence of soluble immune response suppressor. Mice immunized with alloantigen developed two populations of suppressor cells, one of which is antigen nonspecific and inhibitable by anti-soluble immune response antigen nonspecific and inhibitable by anti-soluble immune response suppressor. Soluble immune response suppressor or soluble immune response suppressor-like proteins are produced during various diseases associated with suppressed immune responsiveness including acquired immune deficiency syndrome, schistosomiasis, and nephrotic syndrome. These data suggest that soluble immune response suppressor may have an important physiological role in regulating immune responses and cell division in general (Aune et al., 1982; Aune et al, 1985; Schnaper et al., 1985).

Three biologically active species of soluble immune response suppressor (SIRS) have been isolated at pH7, pH6, and pH5, SIRS-a7, SIRS-a6, and SIRS-a5, respectively, with nearly identical molecular weights of 11,000, when subjected to molecular sieve chromatography. The molecular basis for these isoforms is not clear yet, but it is consistent with earlier studies showing two separate messenger RNA species coding for soluble immune response suppressor (Webb et al., 1985). Soluble immune response suppressor requires a divalent metal ion, probably ferrous iron, for activity, suggesting that soluble immune response suppressor is also a metalloprotein (Schnaper et al, 1989).

Although the complete sequence of soluble immune response suppressor protein is not known, a putative N-terminal 21 amino acid sequence has been obtained for one of the less hydrophobic isoforms, soluble immune response suppressor-a7 (SIRS-a7). The sequence of SIRS-a7 is unique in mammals, but shows a remarkable homology to the family of short neurotoxins, e.g., short neurotoxin 1, found in sea snake, adder, and cobra species. A synthetic polypeptide based on the 21-residue sequence was also prepared and coupled to thyroglobulin or keyhole limpet hemocyanin to prepare rabbit antisera that neutralizes soluble immune response suppressor bioactivity and precipitate soluble immune response suppressor (Webb et al., 1990). Antisera specific for this sequence blocks the suppressive activity of Con A- or IFN-activated suppressor cells (Devens et al., 1988).

There is no conclusive indication from the prior art that soluble immune response suppressor or the putative N-terminal peptide or any variant thereof has therapeutic properties against multiple sclerosis or other autoimmune diseases. Specifically, the prior art is deficient in methods of using soluble immune response suppressor or the N-terminal peptide or any variant thereof as a therapeutic immunomodulator of multiple sclerosis or other autoimmune diseases. The present invention fulfills this long-standing need and desire in the art.

SUMMARY OF THE INVENTION

In some embodiments the current invention is directed to immunotherapeutic compositions. Provided herein is a pharmaceutical composition comprising an immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. As used herein the X variables are defined independently as; X1 is Met, Val, Leu or Cys; X2 is Thr, Ala or Gly; X3 is Glu, Arg, Asp or Lys; X4 is Gln, Ser, Asn or Gly; X5 is Glu, Arg, Asp or Lys; X6 is Ile, Leu, Val, Met or Thr, and X7 is Ala, Cys, Thr or Gly. In certain embodiments X3 is Asp or Glu, and in some cases X5 is Lys or Arg. Thus, in certain embodiments, the polypeptide comprises the amino acid sequence of SEQ ID NO:1. It will also be understood by one of skill in the art that polypeptides having at least about 70%, 75%, 80%, 85%, 90%, 95%, or 100% homology to SEQ ID NO:1 are also included as part of the current invention. In some specific embodiments the polypeptide is SEQ ID NO:1.

The present invention is also directed to a method of immunotherapy in an individual, by administering a immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. In some cases the immunotherapy may be for the treatment of an autoimmune disease in an individual. In some embodiments, the method comprises administering a soluble immune response suppressor peptide having the sequence of SEQ ID NO: 1 or a variant thereof to said individual. The autoimmune disease may be rheumatoid arthritis, psoriasis, type 1 diabetes, SLE, transplant rejection, autoimmune thyroid disease (Hashimoto's disease), sarcoidosis, scleroderma, granulomatous vasculitis, Crohn's disease, ulcerative colitis, Sjögren's disease, ankylosing spondylitis, polymyositis dermatomyositis, polyarteritis nodosa, immunologically mediated blistering skin diseases, Behçet's syndrome, systemic sclerosis, multiple sclerosis, Goodpasture's disease, and immune mediated glomerulonephritis.

The present invention is directed further to a related method of decreasing inflammation associated with an autoimmune disease in an individual. The method comprises administering a immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. This composition may, for example, change a level of an immunosuppressive cytokine, increase a level of at least one anti-inflammatory or a combination thereof.

The present invention is directed further to a method of treating multiple sclerosis in an individual. The method comprises administering a immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. The present invention is further directed to a related method of decreasing the severity of or frequency of a relapse of multiple sclerosis in a human by administering said composition.

The present invention also is directed to a method of increasing the level of an immunosuppressant cytokine in the central nervous system of an individual having multiple sclerosis. Again, the method comprises administering a immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. The peptide or variant increases the level of the immunosuppressive cytokine within the central nervous system of the individual. The present invention is directed further to a related method comprising the additional step of increasing a level of at least one anti-inflammatory cytokine upon increasing the immunosuppressive cycle.

In certain embodiments, the invention is also directed to a method of delaying the onset of an autoimmune disease in an individual. For example, the onset of type 1 diabetes in at-risk individuals may be prevented or delayed by administration of a immunotherapeutically effective amount of a polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other and further aspects, features, and advantages of the present invention will be apparent from the following description of the presently preferred embodiments of the invention. These embodiments are given for the purpose of disclosure.

DETAILED DESCRIPTION OF THE INVENTION

Figure 1:
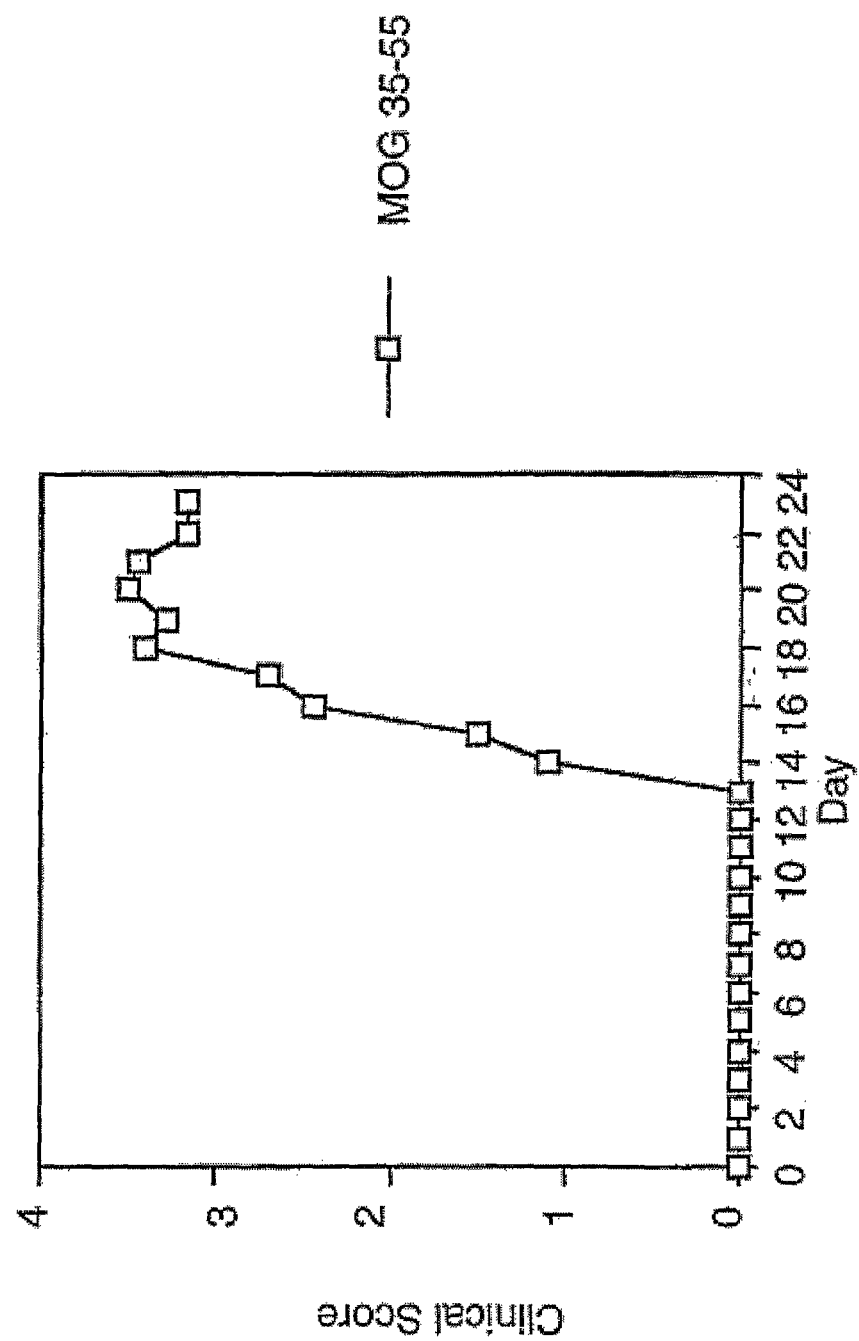
FIG. 1 shows myelin oligodendrocyte glycoprotein peptide 35-55 induces robust acute EAE in B6 mice. Twenty 6-8 week old female C57BL/6 mice were actively immunized by subcutaneous injection of 0.2 ml inoculum containing 200 mg myelin oligodendrocyte glycoprotein peptide 35-55. Clinical severity of the initial attack was graded daily as follows by a blinded observer: 0=no disease, 1=minimal or mild hind limb weakness (associated with limp tail); 2=moderate hind limb weakness or mild ataxia (waddling gait and/or poor righting ability); 3=moderate to severe hind limb weakness, 4=severe hind limb weakness or moderate ataxia; 5=paraplegia with no more than moderate four limb weakness; 6=paraplegia with severe four limb weakness or severe ataxia. The myelin oligodendrocyte glycoprotein peptide-immunized mice reached a mean score of 3.44 on day 21.

In one embodiment of the present invention, there is provided a method of treating multiple sclerosis in an individual, comprising administering immunotherapeutically effective amount of a polypeptide to the individual. The polypeptide comprising the amino acid sequence, X1-X2-X3-X3-X4-X4-X4-X4-X4-X4-Pro-X5-X2-X2-X6-X4-X4-X7-X7-X3-X4 (SEQ ID NO:4) together with a pharmaceutically acceptable carrier. The polypeptide may thus, comprise SEQ ID NO: 1 or a variant thereof. As used herein, "variant" means a protein comprising, a sequence at least about 75, 80, 85, 90, 95, or 100 percent homology to SEQ ID NO: 1. Thus, a SIRS variant comprises a protein, a polypeptide, or a peptide, and may comprise additional amino acids at the amino or carboxyl termini. In all aspects of this embodiment the SIRS peptide or variant thereof may be administered orally or subcutaneously.

In some embodiments, a method of treating an autoimmune disease may comprise delivering a nucleic acid capable of expressing SIRS or a variant thereof to an individual. For example, nucleic acids comprising the sequence of SEQ ID NO: 3 or SEQ ID NO: 5 may be administered to an individual. In some case the expression SIRS, or a variant thereof, may be controlled by an inducible or regulated promoter. Nucleic acids according to the invention may be delivered by any method known to those of skill in the art including, but not limited to, liposomal delivery methods, ballistic methods, and viral vectors.

Thus, expression of the SIRS peptide or variant thereof may induce an immunomodulatory response. In one aspect of this embodiment the immunomodulatory response may be a change in level of at least one immunosuppressive cytokine. Examples of immunosuppressive cytokines are suppressor of cytokine signaling-1 (SOCS-1) and suppressor of cytokine signaling-3 (SOCS-3).

In another aspect the immunomodulatory response is an increase in level of at least one anti-inflammatory cytokine associated with multiple sclerosis. An example of an anti-inflammatory cytokine is interleukin-4. In a related aspect, the immunomodulatory response is a decrease in inflammation associated with multiple sclerosis.

In a related embodiment of the present invention there is provided a method of decreasing the severity or frequency of a relapse of multiple sclerosis in a human comprising administering a soluble immune response suppressor peptide having the sequence of SEQ ID NO: 1 or variant thereof to the individual. Again the SIRS peptide or variant thereof may be administered orally or subcutaneously.

In another embodiment of the present invention there is provided a method of increasing the level of an immunosuppressive cytokine within the central nervous system of an individual having multiple sclerosis, comprising administering a soluble immune response suppressor peptide having the sequence of SEQ ID NO: 1 or a variant thereof to the individual.

Further to this embodiment the method may comprise, increasing a level of at least one anti-inflammatory cytokine upon increasing the level of the immunosuppressive cytokine. An example of an anti-inflammatory cytokine is interleukin-4. In all aspects of this embodiment, the immunosuppressive cytokine is suppressor of cytokine signaling-1 (SOCS-1). Administration of the SIRS peptide or variant thereof is as described supra.

In yet another embodiment of the present invention there is provided a method of treating an autoimmune disease in an individual, comprising administering a soluble immune response suppressor peptide having the sequence of SEQ ID NO: 1 or a variant thereof to said individual.

In one aspect of this embodiment the SIRS peptide or variant thereof decreases inflammation associated with the autoimmune disease. In another aspect, the SIRS peptide or variant thereof changes a level of an immunosuppressive cytokine. Examples of immunosuppressive cytokines are suppressor of cytokine signaling-1 (SOCS-1) and suppressor of cytokine signaling-3 (SOCS-3). In a further aspect, the SIRS peptide or variant thereof increases a level of an anti-inflammatory cytokine. An example of an anti-inflammatory cytokine is interleukin-4.

In all aspects, the SIRS peptide or variant thereof may be administered orally or subcutaneously. Representative autoimmune diseases include rheumatoid arthritis, psoriasis, type 1 diabetes, SLE, transplant rejection, autoimmune thyroid disease (Hashimoto's disease), sarcoidosis, scleroderma, granulomatous vasculitis, Crohn's disease, ulcerative colitis, Sjögren's disease, ankylosing spondylitis, polymyositis dermatomyositis, polyarteritis nodosa, immunologically mediated blistering skin diseases, Behçet's syndrome, systemic sclerosis, Goodpasture's disease, and immune mediated glomerulonephritis.

In a related embodiment, the present invention provides a method of decreasing inflammation associated with an autoimmune disease in an individual, comprising administering a soluble immune response suppressor peptide (SIRS) having the sequence of SEQ ID NO: 1 or a variant thereof to said individual.

Further to this embodiment, SIRS peptide or variant thereof may change a level of an immunosuppressive cytokine, increase a level of at least one anti-inflammatory or a combination thereof. In this further embodiment the immunosuppressive cytokine may be cytokine signaling-1 (SOCS-1) or suppressor of cytokine signaling-3 (SOCS-3). Additionally, the anti-inflammatory cytokine may be IL-4. In one aspect the SIRS peptide or variant thereof may increase the levels of suppressor of cytokine signaling-1 (SOCS-1) and IL-4. In all aspects of this embodiment, the autoimmune diseases and administration of the SIRS peptide or variant thereof are as described supra.

The present invention uses murine experimental autoimmune encephalomyelitis as a model of human multiple sclerosis to deduce the regulation of pro-inflammatory genes by immunomodulatory proteins. Immunization with myelin oligodendrocyte glycoprotein peptide 35-55 (MEVGWYRSPFSRVVHLYRNGK; SEQ ID. NO: 2) induces experimental autoimmune encephalomyelitis, a type IV immune response, in immunocompetent B6 mice. Adoptive transfer of lymphocytes from such mice also induces experimental autoimmune encephalomyelitis in recipient mice.

The soluble immune response suppressor (SIRS) N-terminal peptide 1-21 (MTEENQQSSQPKTTINNAGDS, SEQ. ID NO: 1) demonstrates immunomodulatory activity in both active and passive experimental autoimmune encephalomyelitis. Parenterally administered soluble immune response suppressor peptide 1-21 (SEQ ID. NO: 1) significantly reduced the clinical score of experimental autoimmune encephalomyelitis induced by myelin oligodendrocyte glycoprotein peptide 35-55 (SEQ. ID. NO: 2). Adoptive transfer of lymphocytes from mice immunized with myelin oligodendrocyte glycoprotein peptide 1-21 do not induce experimental autoimmune encephalomyelitis in B6 recipients.

It is contemplated that parenteral soluble immune response suppressor peptides alters the pro-inflammatory signal of encephalitogenic (EAE) lymphocytes at the CNS target tissue. It also is contemplated that adoptive transfer of lymphocytes from soluble immune response suppressor peptide-treated donors will generate anti-inflammatory biological response modifiers in the inflamed CNS, thereby inhibiting disease expression. The soluble immune response suppressor peptide may regulate experimental autoimmune encephalomyelitis by inhibiting the expression of nominal pro-inflammatory cytokines, e.g., inter alia, IFN-γ and TNF-α, inducing the expression of anti-inflammatory cytokines, e.g., inter alia, IL-4, IL-10 or TGF-β or a combination thereof. Thus, genes with a differential expression in treated vs. placebo groups may be candidate genes for modulation by soluble immune response suppressor peptide in experimental autoimmune encephalomyelitis and further in multiple sclerosis or other autoimmune diseases.

It is further contemplated that vital dyes may be used as markers of specific cell populations during adoptive transfer experiments to isolate protective and encephalomyelitic, i.e., effector, cell populations from the CNS target tissue of experimental autoimmune encephalomyelitis in vivo. In addition, microarray techniques can be used to determine unique gene regulation characterizing the protective effect of parenteral soluble immune response suppressor peptide therapy in experimental autoimmune encephalomyelitis.

Thus, the immunomodulatory action of soluble immune response suppressor peptide, as a sole agent or as an adjunct, may be used in the treatment of multiple sclerosis or other autoimmune diseases having an inflammatory component associated with the disease. Examples of such autoimmune disease are rheumatoid arthritis, psoriasis, type 1 diabetes, SLE, transplant rejection, autoimmune thyroid disease (Hashimoto's disease), sarcoidosis, scleroderma, granulomatous vasculitis, Crohn's disease, ulcerative colitis, Sjögren's disease, ankylosing spondylitis, polymyositis dermatomyositis, polyarteritis nodosa, immunologically mediated blistering skin diseases, Behçet's syndrome, systemic sclerosis, Goodpasture's disease, and immune mediated glomerulonephritis.

Thus, the present invention provides a soluble immune response suppressor peptide, such as the N-terminal peptide 1-21 having SEQ ID NO: 1, to treat multiple sclerosis or other autoimmune diseases. The SIRS peptide may decrease inflammation associated with autoimmune diseases as, for example, associated with multiple sclerosis. Additionally, administration of SIRS peptide may decrease the severity of or the frequency of relapse of multiple sclerosis. It is contemplated that the SIRS peptide may be administered to individuals or populations where risk of acquiring the disease may be determined, such as with diabetes, prior to onset of the disease. Furthermore, onset of an autoimmune disease may be delayed in an at-risk individual or population.

Administration of SIRS peptide may change levels of an immunosuppressive peptide such as suppressor of cytokine signaling-1 (SOCS-1) or -3 (SOCS-3) or a combination thereof. Additionally, the level of an anti-inflammatory cytokine, such as, but not limited to, interleukin-4 (IL-4) may be increased. Particularly it is contemplated that the level of SOCS-1 is increased, the level of IL-4 is increased or a combination thereof. The levels of these cytokines may increase in the central nervous system (CNS) tissue, thereby effecting a reduction in associated inflammation as evidenced by reduction in or elimination of clinically apparent symptoms.

It is also contemplated that variants of the SIRS peptide may be used in the practice of the instant invention. These SIRS variants may retain, add to and/or improve upon the immunomodulatory effects of the SIRS peptide. As with the SIRS peptide, SIRS variants may be used therapeutic or as an adjunct. These variants may comprise modified amino acids or may comprise a combination thereof. SIRS variants may be recombinant peptides or chemically synthesized peptides created using recombinant or synthetic methodologies known and standard in the art.

The SIRS peptides or variants thereof may be administered in any manner designed to yield a therapeutic result as described herein. Preferably, these peptides are administered parenterally, such as by subcutaneous injection, or orally, via the alimentary canal by swallowing. Thus, pharmaceutical compositions comprising the SIRS peptide or SIRS variant and a pharmaceutically acceptable carrier, may be administered to an individual having multiple sclerosis or other autoimmune disease. Formulations and compositions for parenteral or oral administration are well known to those of ordinary skill in the art.

Additionally, the SIRS peptides, SIRS variants or pharmaceutical compositions thereof may be administered in an amount to yield a therapeutic immunomodulatory effect. Although an efficacious dose may be any amount encompassed within a range of dosages, such specific amount may depend on any of the particular autoimmune diseases, the stage of the disease as determined, for example, by clinically apparent symptoms, the health and age of the individual with the disease, family history or risk-probability of acquiring the disease. Such specific determination of dose is a standard skill of a practitioner.

The onset or some autoimmune diseases may also be also be delayed by the administration of effective therapy in the preclinical stage of said disease. For example an at-risk population be administered an effective dose of SIRS peptide, or a variant thereof to prevent or delay the onset of said disease. In the case of human IDDM the term "at-risk" populations may comprise for example non-diabetic relatives of IDDM patients with anti-64 kDa autoantibodies including the 65 kD isoform, high titers of islet cell antibodies (ICA), and/or insulin autoantibodies (IAA), in multiplex families with or without blunting of the FPIR (first phase insulin response).

I. A MOUSE MODEL OF MULTIPLE SCLEROSIS

Multiple sclerosis (MS), a chronic inflammatory and demyelinating disease of the central nervous system, has been postulated to be a T-cell mediated autoimmune disease. The disease is thought to be a polygenic disease driven by dysregulation of the immune system leading to an autoimmune response against one or several antigens of cerebral white matter tissue. Multiple sclerosis is clinically associated with periods of disability (relapse) alternating with periods of recovery (remission) but often leading to progressive neurological disability. Multiple sclerosis has been associated with abnormalities of immune regulation.

Studies of the cellular immune system in tissue compartments have suggested that there is a sequestration of antigen-specific T-cell populations in the central nervous system. It has been hypothesized that an influx of such activated autoreactive T cells into the central nervous system leads to inflammation and eventual demyelination, but this mechanism is unproven. Microglia may also play a significant role in multiple sclerosis. The model of acute experimental autoimmune encephalomyelitis (EAE) provides an opportunity to examine the effect of intervention on immunological sensitization.

Adoptive or Passive Transfer of Experimental Autoimmune Encephalomyelitis

Experimental autoimmune encephalomyelitis is a T-cell mediated inflammatory autoimmune process of the central nervous system that resembles in some aspects the human demyelinating disease, multiple sclerosis (Alvord et al., 1965). Experimental autoimmune encephalomyelitis can be passively transferred into naïve syngeneic animals by administration of myelin oligodendrocyte glycoprotein-specific T cells (Lublin, 1985; Peters et al., 1982; Jones et al, 1995). Typical symptoms of experimental autoimmune encephalomyelitis developed after adoptive transfer of myelin oligodendrocyte glycoprotein-sensitized splenic lymphocytes from green fluorescent protein (GFP)-Transgenic mice to irradiated syngeneic C57BL/6 and RAG-1(−/−) mice. Quantitative real-time PCR evaluation indicated that the infiltrating green fluorescent protein expressing T cells exclusively produced T-helper type 1 (Th1)cytokines. Myelin oligodendrocyte glycoprotein-induced nonrelapsing experimental autoimmune encephalomyelitis increased gene expression for both pro-inflammatory and immuno-regulatory cytokines during the course of disease in murine central nervous system.

Synthetic peptide 35-55 from myelin oligodendrocyte glycoprotein (pMOG 35-55) consistently activated encephalitogenic T cells in C57BL/6 (B6) mice. Adoptive transfer of effector myelin oligodendrocyte glycoprotein-specific T cells induced more severe and permanent disease than disease induced by active immunization with pMOG 35-55. Central nervous system lesions in pMOG 35-55 adoptive T-cell-induced experimental autoimmune encephalomyelitis were progressive and more destructive. Myelin oligodendrocyte glycoprotein-specific T cells could be repeatedly re-isolated for up to 287 days from recipient B6 mice in which disease was induced adoptively.

II. A MOUSE MODEL OF TYPE 1 DIABETES

Insulin-dependent diabetes mellitus (IDDM) is a chronic disorder that results from autoimmune destruction of the insulin-producing pancreatic b cell. In the United States, the prevalence of IDDM by age 20 years is 0.26% and lifetime prevalence approaches 0.40%; thus approximately one million Americans have IDDM. Histologic studies suggest that an 80% reduction in the volume of b cells is required to induce symptomatic IDDM. The nonobese diabetic (NOD) mouse is a model of the human autoimmune disease. Many key features of human IDDM are reflected in the NOD mouse model; the development of insulinitis with infiltration of lymphocytes into the pancreatic islets of Langerhans that are selectively cytotoxic to the insulin producing b cells; the dependence of disease pathogenesis by T cells; transmission of IDDM by hematopoietic cells in bone marrow.

The NOD mouse model is mechanistically analogous to the EAE animal model because they are both presumed to be T cell subset mediated, dependent on restriction elements and inflammatory cytokines for disease expression. Although neither acute or chronic EAE have exact parallels to the NOD model, their similarities suggest that interventions successful in EAE can have therapeutic efficacy in the NOD mouse. Both IDDM and EAE can be induced by T cells, primarily one of the two types of helper T cells—T helper cells type 1 (Th1) which produce pro-inflammatory cytokines such as IL-2, IFN-.gamma. or TNF-.alpha. In contrast, administration or up-regulation of the Th2-associated cytokines IL-4 and IL-10 is beneficial and may ameliorate autoimmune disease.

III. PROTEIN EXPRESSION AND PURIFICATION

In a some embodiments of the invention the source of the SIRS peptide may be from cells that are made to over express the protein. For instance cells may be transformed with a nucleic acid vector that expresses SIRS or a precursor thereof. These cells may comprise mammalian cells, bacterial cells, yeast cell, insect cells, whole organisms, or other cells that may be a useful source recombinant protein. The SIRS peptide or SIRS peptide precursor may then be purified from the cells by method know to those of skill in the art.

Thus, in certain embodiments, the invention concerns isolated DNA segments and/or recombinant vectors that encode SIRS. For example set forth in SEQ ID NO: 3 encodes SIRS, and the codons set of this sequence make it useful for expression in eukaryotic cells, for example mammalian or insect cells. On the other hand, the sequence set forth in SEQ ID NO: 5 comprises codons that are optimized for prokaryotic expression of the SIRS peptide.

The term "functionally equivalent codon" is used herein to refer to codons that encode the same amino acid, such as the six codons for arginine and/or serine, and/or also refers to codons that encode biologically equivalent amino acids. For optimization of expression of SIRS in human cells, the codons are shown in preference of use from left to right, in Table 1. The most preferred codon for alanine is thus "GCC", and/or the least is "GCG" (see Table 1, below). While a SIRS encoding nucleic acid sequence useful for expression in mammalian cells is exemplified in SEQ ID NO: 3, essentially any codon in this sequence may be substituted for a different codon that codes for the same amino acid (see Table 1).

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and/or nucleic acid sequences may include additional residues, such as additional N- and/or C-terminal amino acids and/or 5' and/or 3' sequences, and/or yet still be essentially as set forth in one of the sequences disclosed herein. The addition of terminal sequences particularly applies to nucleic acid sequences that may, for example, include various non-coding sequences flanking either of the 5' and/or 3' portions of the coding region and/or may include various internal sequences, i.e., introns, which are known to occur within genes.

Excepting intronic and/or flanking regions, and/or allowing for the degeneracy of the genetic code, sequences that have between about 70% and/or about 79%; and/or more preferably, between about 80% and/or about 89%; and/or even more preferably, between about 90% and/or about 99%; of nucleotides that are identical to the nucleotides of SEQ ID NO: 3 and/or SEQ ID NO: 5 will be sequences that are "essentially as set forth in SEQ ID NO: 3 and/or SEQ ID NO: 5".

In some cases it may be preferable that the recombinant SIRS coding sequence be fused with additional amino acid sequence. For example, expressed protein may be tagged for purification. Some possible fusion proteins that could be generated include histadine tags, Glutathione S-transferase (GST), Maltose binding protein (MBP), Flag and myc tagged SIRS. These additional sequences may be used to aid in purification of the recombinant protein, and in some cases may then be removed by protease cleavage. For example coding sequence for a specific protease cleavage site may be inserted between the SIRS coding sequence and the purification tag coding sequence. One example for such a sequence is the cleavage site for thrombin. Thus fusion proteins may be cleaved with the protease to free the SIRS peptide or peptide derivative from the purification tag. In further embodiments, recombinant SIRS protein or SIRS precursors may be further comprise a secretion signal that allow the recombinant protein to be secreted from expressing cells. Thus in some embodiments, SIRS or SIRS precursors may be purified from the media of expressing cells.

Any of the wide variety of vectors known to those of skill in the art could be used to express or over express proteins according to the invention. For example, plasmids, phagmids or viral vectors may be used. In certain embodiments vectors for expression of SIRS or a variant thereof may comprise a promoter sequence. In some applications the promoter sequence may be a regulated or inducible promoter. In applications in which eukaryotic expression vectors are used the vector may further comprise a poly-adenylation signal sequence. It is well understood to these of skill in the art that these vectors may be introduced in to cells by a variety of methods including but not limited to, transfection (e.g, by liposome, calcium phosphate, electroporation, particle bombardment, etc.), transformation, and viral transduction. In some additional embodiments, the expression vectors of the invention may be stably maintained in cells. For example the expression region may be integrated into the genomic DNA of the expressing cell. Alternatively or additionally, the expression vector may further comprise drug resistance marker that allow selection of cells that express the vector by treatment of a cell population with said drug.

In certain embodiments it is also contemplated that SIRS peptide or a variant thereof may be chemically synthesized, and purified by methods know to those in the art.

IV. VARIATION OF AN AMINO ACID CODING REGION

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *-0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred. Thus, as used herein the term "percent homology" refers to a comparison between amino acid sequences, for example wherein amino acids with hydrophilicities within +/−1.0, or +/−0.5 points are considered homologous.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

V. PHARMACEUTICAL COMPOSITIONS

Pharmaceutical compositions of the present invention are also contemplated. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition including the SIRS peptide or a variant thereof will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated.

In certain embodiments compositions comprising SIRS peptide or a derivative thereof may be delivered as a liposomal composition. For example, the SIRS peptide or SIRS derivative may be presented on the surface of or be encapsulated within a liposome. As used herein the term "liposome" refers to a lipid composition comprising one or more concentric layers of lipid molecules. Liposomes may be cationic, anionic or neutral, and in some cases liposomes may be stabilized by the addition of protein and/or additional lipids or cholesterol. For example liposomes may be prepared in accordance with known laboratory procedures such as those disclosed in Bangham et al. (1965), Gregoriadis (1979), Deamer and Uster (1983), or Szoka and Papahadjopoulos (1978), the contents of which are each incorporated herein by reference.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alternatively, a patient may be given $1\times10^{-5}$, $10^{-6}$, $10^{-6}$, $10^{-7}$, $10^{-8}$, $10^{-9}$, $10^{-10}$, $10^{-11}$, $10^{-12}$ M of a substance (or any range derivable therein), the SIRS peptide or a derivative thereof, in a volume of 0.1 µl, 1.0 µl, 10 µl, 100 µl, 1 ml, 5 ml, 10 ml, 20 ml, 25 ml, 50 ml, 100 ml, 200 ml, 300 ml, 400 ml, 500 ml, or more (or any range derivable therein). Inhibitors may be administered 1, 2, 3, 4, 5, 6, 7, 8, 9, 10 or more times over a course of 1, 2, 3, 4, 5, 6, 7, 8, 9 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, or 1, 2, 3, 4, 5, 6, 7, 8, 9, 10 or more years on a regular or as needed basis.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may comprise different types of carriers depending on whether it is to be administered in solid, liquid or aerosol form, and whether it need to be sterile for such routes of administration as injection.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

VI. ROUTES OF ADMINISTRATION

Compositions of the present invention may be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

In certain embodiments compositions of the invention may be delivered orally in the form of a caplet. In some cases the caplet may dissolve so as to deliver compositions of the invention distal portions of the gut epithelia. For example, delivery of compositions comprising SIRS peptide or derivatives thereof in coated caplets may allow delivery to immunologically important sites in the small intestines such as the Peyer's Patches.

VII. COMBINATION THERAPIES

In order to increase the effectiveness of a treatment with the compositions of the present invention, it may be desirable to combine these compositions with other therapies effective in the treatment of specific diseases or conditions.

The compositions of the present invention can precede or follow the other agent treatment by intervals ranging from minutes to weeks. It is contemplated that one may administer both modalities within about 12-24 h of each other and, more preferably, within about 6-12 h of each other. In some situations, it may be desirable to extend the time period for treatment significantly, where several days (2, 3, 4, 5, 6 or 7) to several weeks (1, 2, 3, 4, 5, 6, 7 or 8) lapse between the respective administrations.

Various combinations may be employed where a composition including a nucleic acid of the invention inhibitor is "A" and the secondary agent, is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

For example, compositions comprising SIRS peptide or a derivative thereof may be used in combination with alpha interferon as described in U.S. Patent Application No. 20040151694. In certain cases, compositions according to the invention may be used in combination with steroids.

VI. EXAMPLES

The following examples are given for the purpose of illustrating various embodiments of the invention, and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages herein. Changes therein and other uses which are encompassed within the spirit of the invention as defined by the scope of the claims will occur to those skilled in the art.

Example 1

Myelin Oligodendrocyte Glycoprotein Peptide 35-55 Induces Robust Acute EAE in B6 Mice Twenty 6-8 week old female C57/BL6 mice (Jackson Labs, Bar Harbor, Me.) were actively immunized on days 0 and 7 by subcutaneous injection (s.c.) with 0.2 ml inoculum containing 200 mg myelin oligodendrocyte glycoprotein peptide 35-55 [Met Glu Val Gly Trp Tyr Arg Ser Pro Phe Ser Arg Val Val His Leu Tyr Arg Asn Gly Lys, (SEQ ID NO: 2)] in IFA (Difco Labs, Detroit, Mich.) and 800 mg *Mycobacterium tuberculosis hominis* H35Ra. Pertussis toxin (200 ng) was injected i.p. on days 0 and 2.

Clinical severity of the initial attack was graded daily as follows by a blinded observer. 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia. The myelin oligodendrocyte glycoprotein peptide-immunized mice reached a mean score of 3.44 on day 21 (FIG. 1).

Example 2

Figure 2:
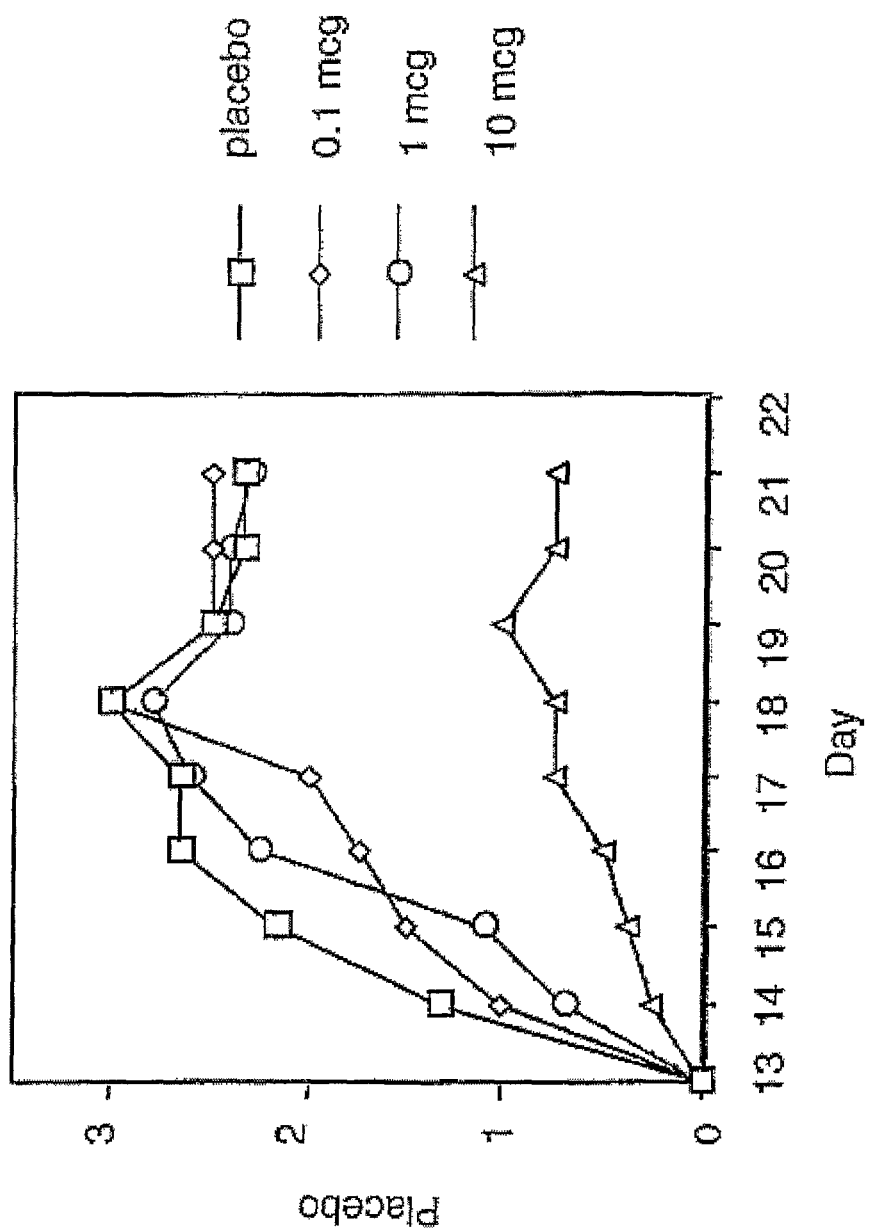
FIG. 2 shows inhibition of acute EAE in B6 mice by soluble immune response suppressor peptide 1-21. B6 mice were immunized with myelin oligodendrocyte glycoprotein peptide 35-55 on day 0 as described above. On day −7 preceding active immunization, and continuing through day +14 post immunization, B6 mice (n=8/group) were injected with 0.1 ml of control saline, 0.1, 1, or 10 mg of soluble immune response suppressor peptide 1-21. Ten mg of soluble immune response suppressor peptide 1-21 showed a significant inhibition of disease severity compared to a placebo, 0.1 and 1 mg dosing ($p<0.001$).

Parenteral Soluble Immune Response Suppressor Peptide 1-21 Inhibits Acute EAE in B6 Mice B6 mice were immunized with myelin oligodendrocyte glycoprotein peptide 35-55 on day 0 as described above. On day −7 preceding active immunization, and continuing through day 14 post immunization, B6 mice (n=8/group) were injected with 0.1 ml of control saline, 0.1, 1, or 10 mg soluble immune response suppressor peptide 1-21 [Met-Thr-Glu-Glu-Asn-Gln-Gln-Ser-Ser-Gln-Pro-Lys-Thr-Thr-Ile-Asn-Asn-Ala-Gly-Asp-Ser, (SEQ ID. NO: 1)]. FIG. 2 shows that 0.1 and 1 mg soluble immune response suppressor peptide had no significant inhibition of EAE compared to placebo. However, 10 mg of soluble immune response suppressor peptide 1-21 showed a significant inhibition of disease severity compared to placebo, 0.1 and 1 mg dosing ($p<0.001$). Soluble immune response suppressor peptide 10 mg s.c. showed a dose-response effect with doses <10 mg not showing a clinically significant effect.

Example 3

Adoptive Transfer of Lymphocytes from Soluble Immune Response Suppressor Peptide-Injected Donors Protects Against EAE in B6 Recipients B6 mice effector donors were actively immunized with myelin oligodendrocyte glycoprotein peptide 35-55 described above (day 0) and injected (day −7 through day +14 post-immunization) with 0.1 ml of control saline (n=8) or 10 mg of soluble immune response suppressor peptide 1-21 (n=8). On day 14 post inoculation, splenocytes from both saline-injected (mock control) and soluble immune response suppressor peptide-injected (active treatment) immunized donor mice were re-stimulated in vitro with 30 mg/ml myelin oligodendrocyte glycoprotein peptide 35-55 at $20 \times 10^6$ splenocytes for >1 hour and then diluted to 2-4 million cells/ml and cultured for 48-72 hours in RPMi with 10% FCS and 1% Pen/Strep. Myelin oligodendrocyte glycoprotein-restimulated cells were washed, counted and passively transferred ($10 \times 10^6$) i.p. into 8-10 week old female B6 recipients.

Figure 3:
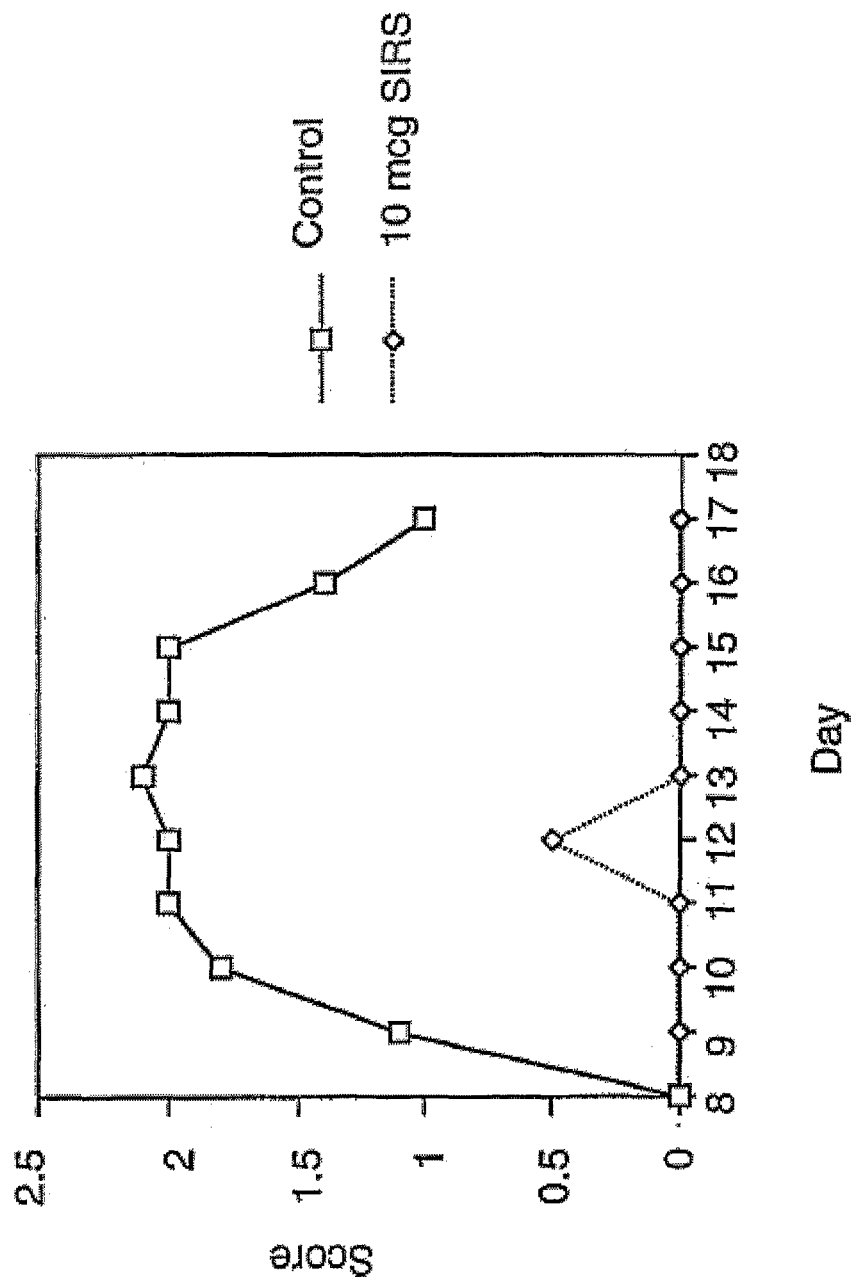
FIG. 3 shows soluble immune response suppressor peptide injected donor cells do not adoptively transfer EAE to B6 immunocompetent recipients. B6 mice effector donors were actively immunized with myelin oligodendrocyte glycoprotein peptide 35-55 described above (day 0) and injected (day −7 through day +14 post-immunization) with 0.1 ml of control saline (n=8) or 10 mg of soluble immune response suppressor peptide 1-21 (n=8). On day 14 post inoculation, splenocytes from both saline-injected and soluble immune response suppressor peptide-injected immunized donor mice were re-stimulated in vitro with myelin oligodendrocyte glycoprotein peptide 35-55 and passively transferred ($10 \times 10^6$) i.p. into 8-10 week old female B6 recipients. B6 recipients (control group) receiving donor splenocytes from saline-injected donors experienced onset of clinical disease at 9 days post passive immunization. In contrast, B6 recipients receiving splenocytes from soluble immune response suppressor peptide-injected donors did not have any prolonged clinical disease during this time period.

As shown in FIG. 3, B6 recipients (control group) receiving $10 \times 10^6$ myelin oligodendrocyte glycoprotein-activated splenocytes from saline-injected donors experienced onset of clinical disease at 9 days post passive immunization. The control group reached a maximum disease score of 2.1. In contrast, B6 recipients receiving $10 \times 10^6$ myelin oligodendrocyte glycoprotein-activated splenocytes from soluble immune response suppressor peptide-injected donors did not have any prolonged clinical disease during this time period.

Taken together, the above data show that myelin oligodendrocyte glycoprotein peptide 35-55 can induce experimental autoimmune encephalomyelitis in B6 mice and active experimental autoimmune encephalomyelitis can be successfully inhibited with adequate amounts of soluble immune response suppressor peptide. Soluble immune response suppressor peptide-treated donor cells do not adoptively transfer EAE to B6 immunocompetent recipients, indicating soluble immune response suppressor peptide 1-21 alters myelin oligodendrocyte glycoprotein-specific effector cells and renders these cells incapable of adoptively transferring the disease.

Previous data from the soluble immune response suppressor literature suggests that soluble immune response suppressor acts via $CD8^+$ T cells. Therefore, immunization and adoptive transfer experiments as described above can be performed with mitogen or antigen-activated $CD8^+$ T cells to determine whether $CD8^+$ T cells from soluble immune response suppressor peptide-treated donors can protect against experimental autoimmune encephalomyelitis induction.

Example 4

Ingested Soluble Immune Response Suppressor Peptide 1-21 Inhibits Acute EAE in B6 Mice The following experiments examined the immunomodulatory capability of ingested, i.e., orally administered to the gut, soluble immune response suppressor peptide to experimental autoimmune encephalomyelitis. B6 mice were immunized with myelin oligodendrocyte glycoprotein peptide 35-55 on day 0 as described above. On day −7 preceding active immunization and continuing through day 14 post immunization, B6 mice (n=4/group) were gavaged with 0.1 ml of control saline, 0.1, 1, 10 or 100 mg of soluble immune response suppressor peptide 1-21.

Figure 4:
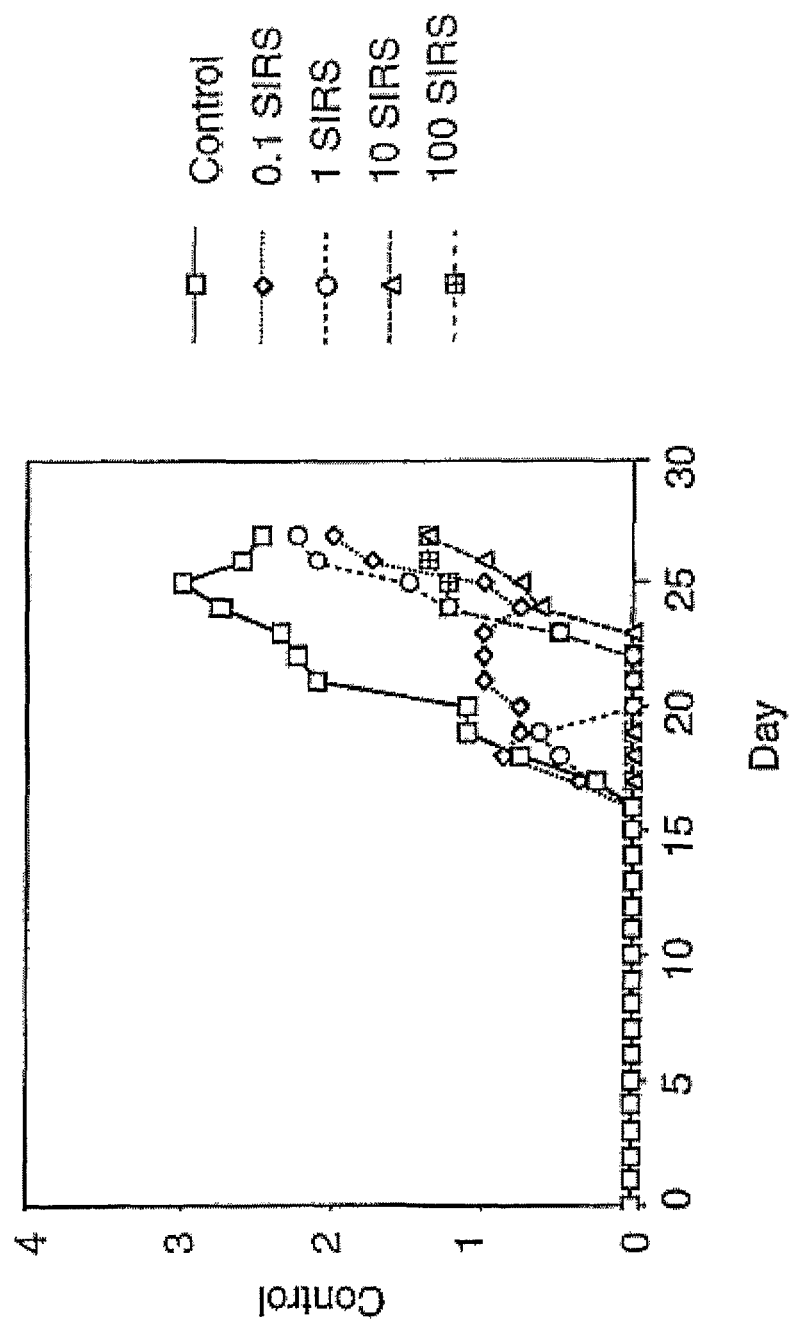
FIG. 4 shows ingested soluble immune response suppressor peptide 1-21 inhibits acute EAE in B6 mice. B6 mice were immunized with myelin oligodendrocyte glycoprotein peptide 35-55 on day 0 as described above. On day −7 preceding active immunization, and continuing through day 14 post immunization, B6 mice (n=4/group) were gavaged with 0.1 ml of control saline 0.1, 1, 10 or 100 mg of soluble immune response suppressor peptide 1-21. 0.1 mg ($p<0.001$) and 100 mg ($p<0.005$) of soluble immune response suppressor peptide 1-21 not only showed a significant inhibition of disease severity but also a prolonged delay in the onset of disease compared to placebo.

FIG. 4 shows that 0.1 mg ($p<0.011$, t-test) and 1 mg ($p<0.009$, t-test) of soluble immune response suppressor peptide had significant inhibition of experimental autoimmune encephalomyelitis compared to placebo overall ($p<0.01$, t-test two tailed). However, 10 mg ($p<0.001$) and 100 mg ($p<0.005$) of soluble immune response suppressor peptide 1-21 not only showed a significant inhibition of disease severity but also a prolonged delay in the onset of disease compared to placebo.

Figure 5:
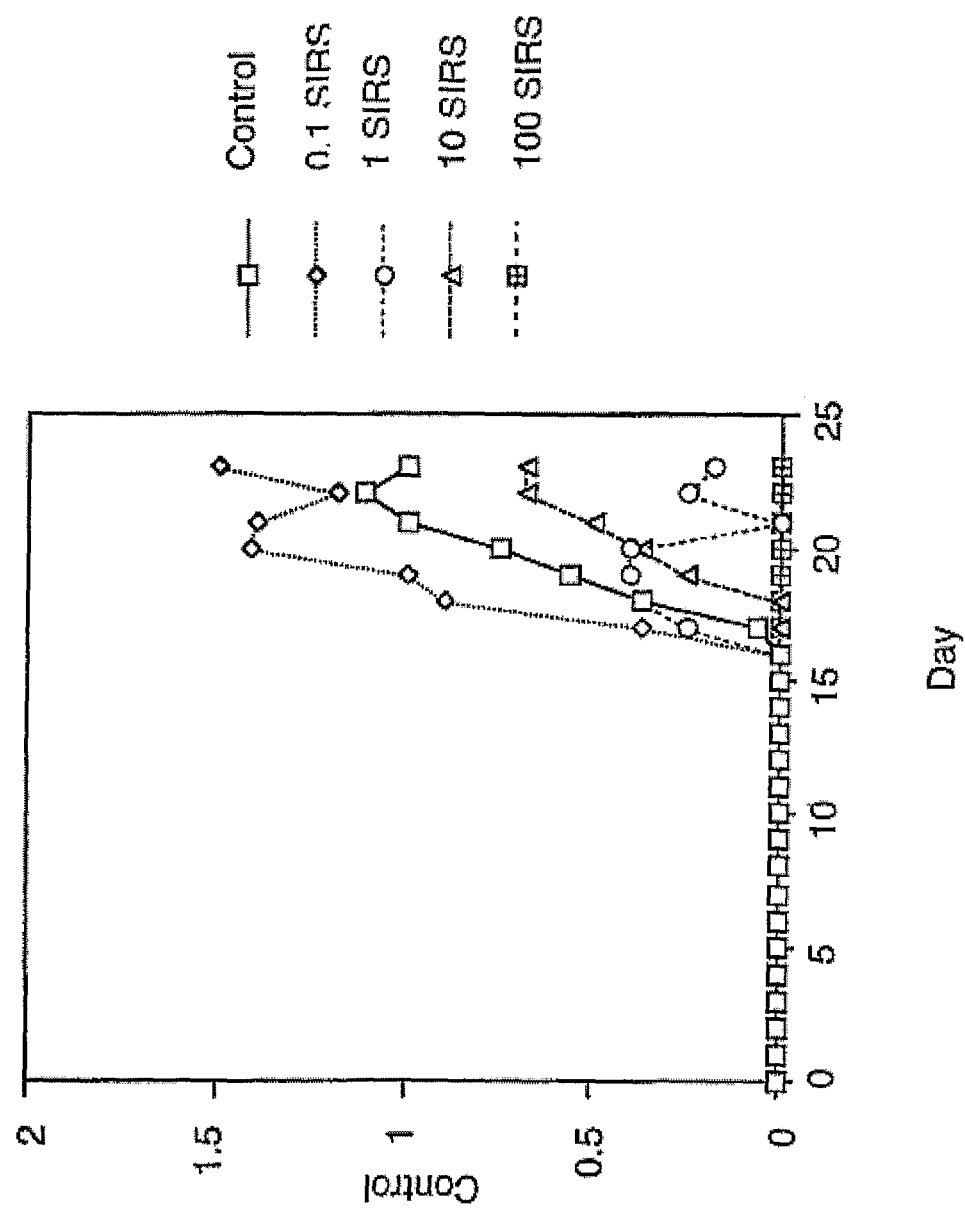
FIG. 5 is a repeat experiment of FIG. 4. One mg ($p<0.038$, Mann-Whitney) and 100 mg ($p<0.001$) of soluble immune response suppressor peptide 1-21 showed a significant inhibition of disease severity and a prolonged delay in the onset of disease compared to placebo.

In a repeat experiment, B6 mice were immunized (n=4/group) and gavaged as described above. FIG. 5 shows that 0.1 mg of soluble immune response suppressor peptide had no significant inhibition of experimental autoimmune encephalomyelitis compared to placebo overall. However 1 mg ($p<0.038$, Mann-Whitney) and 100 ($p<0.001$) soluble immune response suppressor peptide 1-21 showed a significant inhibition of disease severity and a prolonged delay in the onset of disease compared to placebo. These data indicate that ingested soluble immune response suppressor peptide shows a dose-response effect with 100 mg showing the most profound clinical effect in repeat experiments.

Example 5

Quantitative PCR Assay

Cytokine production by stimulated lymphocytes in vitro may not reflect in vivo activity. Ex vivo analysis avoids the problems of in vitro restimulation with antigen or mitogen. As such, cytokine production from central nervous system tissue samples measurable by ELISA may not accurately reflect the activity of the cells in vivo. Quantitative PCR analysis for cytokine mRNA in cell samples taken directly from target central nervous system tissue can circumvent this problem.

Quantitative PCR can be performed for nominal EAE cytokine or transcript of interest. In particular, the mean measured transcript levels for IL-2/IFN-γ (Th1-like), IL-4/IL-10 (Th2-like) and other nominal biologic response modifiers of interest (e.g. TGF-β, IL-1, IL-6, IL-12, TNF-α) will be normalized to the b-actin control and expressed as % b-actin molecules. Demonstration of increased nominal anti-inflammatory or decrease pro-inflammatory biological response modifiers in the central nervous system tissue by quantitative PCR would be highly suggestive that alterations of nominal effector (encephalitogenic) factors at the site of inflammation are the results of soluble immune response suppressor peptide induced-protective cells.

Real-time quantitative PCR, which is based on the use of fluorescent probes to continuously monitor the progress of PCR reaction, would provide high throughput transcript analysis. Traditional fixed-cycle PCR is difficult to use as a quantitative assay because of the need to analyze multiple PCR cycles to gather data only from the exponential phase of the amplification reaction and the difficulty in measuring the product formed in each reaction. An integrated thermocycler/fluorometer (ABI 7700 Sequence Detector System) has been introduced that simultaneously monitors progress of PCR reactions in a 96-well format.

The system is based on the endonuclease activity of Taq polymerase to hydrolyze oligonucleotides hybridized to a template undergoing replication. The amplification reaction includes a template, conventional forward and reverse PCR primers and a specific hybridization probe derivatized with two dyes (reporter-FAM and quencher TAMRA) that are quenched by intramolecular energy transfer. During the PCR reaction, Taq hydrolyses the probe that is bound to the template, liberating the reporter dye from the quencher and producing an increase in reporter dye fluorescence. Each PCR cycle results in an increase in fluorescent signal that is directly proportional to the number of probe molecules being hydrolyzed which, in turn, is a direct measure of the number of template amplicons present in the reaction during that cycle. The ABI7700 Sequence Detector has a multiplexed laser and CCD detector that allows for continuous measurement of fluorescent signal present in each PCR reaction tube in a 96 well plate.

The Ct., i.e., the number of PCR cycles required for the fluorescent signal to reach an arbitrary threshold, is directly proportional to the amount of input template so that with the use of appropriate sRNA standards, one can calculate the number of template molecules introduced into the reaction. Traditional competitive quantitative PCR generally bases quantitation on an internal standard "spiked" into the unknown sample. In contrast, real-time quantitative PCR bases quantitation on a set of sRNA standards run in parallel in separate wells in the 96-well plate. Using sRNA standards with a known number of template molecules, interpolation of the Ct. of the "unknown" samples into the standard curve allows for the calculation of absolute number of template molecules in the "unknown" sample.

Example 6

Quantitative PCR Determination of Cytokines and Biologic Response Modifiers

Inflamed spinal cords from soluble immune response suppressor peptide-fed B6 mice (active treatment group) or from mock fed donor mice (control) were utilized for the experiments below. Intact spinal cord can be ejected by injecting saline into the distal end of the spinal canal and stored in RNALater (Ambion). The spinal cord is disrupted and the resulting cell suspension is filtered through a Falcon Cell Strainer 2350 (Becton Dickinson, San Jose, Calif.). Total RNA was processed on day 23-26 post active immunization, and relative numbers of transcripts for IFN-γ, IL-4, IL-10, SOCS-1, SOCS-2, and SOCS-3 were determined by quantitative PCR. The measured mean transcript levels were normalized to b-actin control (normalization mean=COI mean/b-actin×100) and expressed as % b-actin molecules.

Suppressors of cytokine signaling, SCOS, consist of eight members (SOCS-1 to SOCS-7 and CIS). Expression of SOCS-1, SOCS-2 and SOCS-3 is induced by various cytokine and overexpression studies in various cell lines have demonstrated their inhibitory roles. These family members have been implicated in negative regulation of several pathways, particularly the JAK/STAT pathway. In gene modification studies in mice, it has been demonstrated that SOCS-1 plays an important role in IFN-γ regulation and T cell differentiation, while SOCS-2 seems necessary for normal growth regulation. Treatment with conditioned medium from myelin basic protein-stimulated encephalitogenic lymphoid cells induced SOCS-1 expression. SOCS-1 and SOCS-3 also inhibit interleukin-4-dependent signal transduction.

Results shown in Tables 2 and 3 indicate that there are clear differences in the levels of pro-inflammatory SOCS-1, SOCS-3 and IL-4 either in the peripheral immune system (spleen) or more importantly in the CNS target tissue (spinal cord) of soluble immune response suppressor peptide-fed mice compared to saline (mock)-fed mice. There were significant decreases in (underlined) SOCS-1 (up to 30%) and SOCS-3 (60%) in splenic samples from soluble immune response suppressor peptide-fed mice compared to control (bolded). There was no significant difference in SOCS-2, IL-4, IL-10 or IFN-γ in these splenic samples (data not shown).

In contrast to the peripheral immune system, in the CNS target organ where myelin oligodendrocyte glycoprotein-specific T and other activated cells migrate and cause experimental autoimmune encephalomyelitis, there is a significant increase in SOCS-1 gene expression after feeding with soluble immune response suppressor. Administration of soluble immune response suppressor peptide increased (underlined) SOCS-1 expression by 75-175% of control (bolded). This may be the primary mode of immunomodulation by the soluble immune response suppressor peptide.

The significance of the decrease in SOCS-3 by 45% in the CNS target organ is unclear, but clearly shows another immunomodulatory effect of ingested soluble immune response suppressor peptide. The significance of the decrease in IL-4 expression by up to 80% in the CNS target organ is likely related to SOCS-1-induced inhibition of IL-4 dependent signal transduction and clearly shows another immunomodulatory effect of ingested soluble immune response suppressor peptide. There were no significant differences in SOCS-2, IL-10, or IFN-γ in these cord samples.

In summary, these data show that 1) quantitative PCR can detect SOCS-1, SOCS-3 and IL-4 transcripts in spleen and/or CNS, 2) quantitative PCR-detected genes differentiate control from active treatment groups according to their clinical outcomes and can detect and differentiate groups as late as 23-26 days after immunization, and 3) the presence of higher expression levels of SOCS-1 in the CNS of protected mice may be the critical mediator of the soluble immune response suppressor peptide effects and correlates best with amelioration of clinical disease expression.

Quantitative PCR can also be performed on cell samples obtained from mice receiving adoptively transferred spleen cells from soluble immune response suppressor-treated mice. Myelin oligodendrocyte glycoprotein peptide 35-55-immunized B6 mice can be treated for at least 21 consecutive days (day −7 to day +14 post-immunization) with either 10 mg of soluble immune response suppressor peptide (n=20) (active treatment group) or with saline s.c. (control group). Spleen cells are harvested, restimulated in vitro as described above and $\geq 10-30\times10^6$ splenocytes are transferred to B6 immunocompetent recipients (day 0). Alternatively, naïve B6 female mice (6-8 weeks old) can be treated for at least 14 consecutive days with saline (n=20) or 10 mg of soluble immune response suppressor peptides s.c. (n=20). Spleen cells harvested from the treated animals are then stimulated with Con A (2.5 mg/ml) for ≥48 hours and transferred ($10-30\times10^6$) to B6 immunocompetent recipients (day 0).

TABLE 2

Soluble Immune Response Suppressor Peptide-Fed Mice Generate Less Splenic SOCS-1 and SOCS-3 Compared to Placebo-Treated Mice

| Treatment | SOCS-1 | SOCS-3 |
|---|---|---|
| Control | 0.33 | 0.45 |
| 0.1 mg | 0.28 | 0.38 |
| 1 mg | 0.30 | <u>0.28</u> |
| 10 mg | <u>0.23</u> | <u>0.21</u> |
| 100 mg | <u>0.23</u> | <u>0.18</u> |

TABLE 3

Soluble Immune Response Suppressor Peptide-Fed Mice Generate More SOCS-1, Less SOCS-3 and IL-4 in CNS Target Tissue Compared to Placebo-Treated Mice

| Treatment | SOCS-1 | SOCS-3 | IL-4 |
|---|---|---|---|
| Control | 0.08 | 0.39 | 0.15 |
| 0.1 mg | 0.14 | 0.45 | 0.04 |
| 1 mg | 0.19 | 0.54 | 0.15 |
| 10 mg | 0.22 | 0.28 | 0.05 |
| 100 mg | 0.14 | 0.22 | 0.02 |

Example 7

Cell Migration Studies

The contribution of soluble immune response suppressor peptide-activated lymphocytes to the modulation of EAE can be examined in immunocompetent recipients by labeling passively transferred cells populations with vital dyes. The transferred cells, along with endogenous cells from the recipient, will migrate to the CNS target tissue. Labeled cells can then be isolated from the CNS and spleen of recipient mice. FACS sorting will further distinguish unique effector, protective and endogenous cell populations isolated from inflamed spinal cord. These specific populations can be examined for changes in biological response modifiers pre- and post adoptive transfer. Determination of effector cell numbers of the respective labeled cell populations at various times after adoptive transfer also addresses whether inhibition of experimental autoimmune encephalomyelitis correlates with decreased infiltration of effector cells into the CNS or altered biological response modifier production with significant effector cell infiltration.

Lymphocyte migration studies require stable dyes that can be visualized in tissue days or weeks after adoptive transfer. Several vital dyes have been investigated for their utility in migration studies. The vital dye 5- (and 6-) carboxyfluorescin diacetate succinimidyl ester (CFSE) (Molecular Probes, Eugene, Oreg.), a fluorochrome which can covalently couple with intracellular macromolecules on lymphocytes, can be readily detected for up to 11 weeks post i.v. injection. Alternatively, fluorescein-labeling molecule PKH26 (Zynaxis, Malvern, Pa.) incorporated into the lipid bilayer of cytoplasmic membranes can be easily detected in various tissues after 6-28 days of in vivo circulation.

CM-Dil lipophilic is another marker that intercalates in the plasma membrane like the PKH dyes. CM-Dil can be fixed using traditional aldehyde fixatives, making it feasible to detect labeled cells in histological sections. CM-Dil is retained in the lymphocyte membrane and does not alter the process of lymphocyte recirculation. These vital dyes provide useful markers for isolation of effector (EAE) and protective (soluble immune response suppressor-induced) cells from inflamed CNS in the presence or absence of soluble immune response suppressor peptide therapy.

Example 8

Microarray Analysis

The development of rational strategies for the treatment and prevention of multiple sclerosis, particularly for reducing risks of disease progression, will benefit greatly from an improved understanding of basic aspects of experimental autoimmune encephalomyelitis models. Microarray technology can be used to discover unique transcripts or biomarkers relevant to the therapeutic effects of parenteral soluble immune response suppressor peptide treatment. Previous studies have found that of the approximately 11,000 mouse genes studied, 213 were regulated differentially and 100 showed consistent differential regulation in experimental autoimmune encephalomyelitis. Of the 104 genes with defined chromosomal locations, 51 were mapped to known experimental autoimmune encephalomyelitis-linked quantitative trait loci and as such were putative candidate genes for susceptibility to experimental autoimmune encephalomyelitis.

A general strategy of microarray expression profiling involves using pooled RNAs from different treatment groups for microarray experiments and then using quantitative PCR assays on RNAs from individual animals within each treatment group to validate the results. RNA prepared from CNS infiltrating lymphocytes from individual animals from the different treatment groups was used to identify candidate biomarker genes. A double label, differential hybridization system (two color system) on high density spotted cDNA microarrays (Agilent mouse cDNA microarrays—20,000 cDNAs per chip) can be used to identify transcripts subject to differential expression between soluble immune response suppressor peptide-treated and control mice. To maximize the recovery of information and minimize the number of arrays necessary to analyze this multivariate experimental design, RNAs from each of the treatment groups is analyzed against a common standard mouse RNA (from Stratagene).

The experimental protocol is as follows. Two separate pools of RNA are prepared from each of the 2 treatment groups. These duplicate pools are then used to prepare mRNA. Cy-3 and/or Cy-5 cDNAs generated from these mRNA by an indirect labeling protocol (Amersham) are mixed with a Cy-5, or Cy-3, labeled standard mouse cDNA and the resulting dual label cDNA mixture is hybridized to an Agilent mouse cDNA microarray according to the manufacturer's recommended procedure.

The washed chips are read with a Packard GSI Lumonics chip reader and the digital image output analyzed using commercially available software (ImageQuant). Analysis of multiple arrays and pattern recognition can be carried out using GeneSpring (Silicon Genetics). The duplicate pools from each group are analyzed separately. If necessary, individual pools can be analyzed with reversed dyes to eliminate dye-labeling artifacts. Analyzing the 2 treatment groups requires a minimum of 3 Agilent chips, realistically 6, allowing for repeat runs and dye reversals.

The data sets generated by these studies can be used to address a number of potentially important questions about the impact of intervention on experimental autoimmune encephalomyelitis gene expression. Of specific interest is the identification of genes that may be useful biomarkers for the effects of soluble immune response suppressor peptide on experimental autoimmune encephalomyelitis gene expression. To address this question, two large data sets of experimental autoimmune encephalomyelitis genes are identified: soluble immune response suppressor (SIRS)-independent genes, i.e., all the genes detected on the microarrays whose expression is not altered by SIRS, and SIRS-regulated genes, i.e., all those genes whose expression is reproducibly altered by the soluble immune response suppressor in the treatment group.

Microarray studies have the potential to produce very large amounts of interesting information, but without independent validation and confirmation it is hard to assess the reliability of the results. An approach to validation is to first set criteria for the selection of specific candidate genes that merit further investigation and validation. Real-time quantitative PCR assays can then be designed for these transcripts and measure the levels of their expression in experimental autoimmune encephalomyelitis RNAs, along with beta-actin mRNA as a normalizer, obtained from individual animals in each treatment group.

This approach allows for the acquisition of sufficient amounts of accurate transcript data to determine whether the transcript of interest is or is not differentially expressed under the condition of interest. The criteria used to select candidate transcripts include: (1) genes with known homologous human sequences are given priority over ESTs or mouse genes without a known human counterpart; (2) genes with functions related to immune-related molecules, extracellular matrix and cell adhesion molecules, molecules involved in cell division and transcription and differential regulation of molecules involved in signal transduction, protein synthesis, and metabolism are given priority over genes of unknown or irrelevant biological functions; and (3) genes showing robust alterations in their level of expression (>2-fold) in treated versus untreated animals are given priority over genes with lesser inductions or suppressions.

Based on these criteria, up to 20 soluble immune response suppressor peptide-regulated candidate protective biomarkers can be selected. Forward and reverse primers with very short amplicons (<80 nt) are designed (using Primer Express, ABI) for the transcripts that are selected for validation. The primers are designed for compatibility with the Cyber green amplicon detection system.

For Cyber green assays that are problematic, usually from low signal to noise, high baselines, high background, poor efficiency of amplification, suitable fluorescent probe (Taqman) assays can be designed. Total RNA (40 ng samples assayed in triplicate) from individual animals is assayed by real-time quantitative PCR. The PCR assays can be run in a 96-well format using an ABI 7700 Sequence detector so that a single plate can readily accommodate the 12 RNA samples, plus internal standards and controls, required for comparison of two treatment groups. An intra-assay coefficient of variability of 15% and an inter-assay CV of <30% would enable detection of 2-fold or greater differences between samples (n=12) with confidence ($p<0.5$).

Example 8

NOD female mice (NOD MrkTacfBR) were obtained from Taconic Farms at eight weeks of age and feeding with mock (n=12) or 100 μg SIRS peptide 1-21 (n=6) in 0.1 ml DPBS daily was initiated at ten weeks. One hundred micrograms was used because this was an effective dose for inhibiting EAE (experimental autoimmune encephalomyelitis) in mice. The mice were maintained and fed under SPF conditions in microisolators, and handled under negative pressure sterile hoods. Surveillance mice were maintained with experimental mice and examined regularly for routine murine pathogens.

Mice were followed after initiation of feeding by weekly blood glucose determination (Life Scan One Touch II, Johnson & Johnson) beginning at week 18 thru 22. Animals were considered diabetic if two consecutive blood glucose determinations were above >11.1 mmol/l or >200 mg/ml. Spontaneous diabetes (blood sugar >11.1 mmol/l; >200 mg/ml) occurs in 50% female NOD mice by age 19 weeks in our facility.

Mock or SIRS peptide 1-21 was administered using a 2.5 cm syringe fitted with a 22-24 gauge ball point needle directly to the stomach and proximal small intestine (Thomas Scientific, Swedesboro, N.J.) daily to NOD mice beginning at age ten weeks. The peptide was directly delivered to the distal esophagus, stomach and proximal small intestine (as determined experimentally by injecting Evans blue during routine feeding and subsequent sacrifice). Disease course was plotted as Kaplan-Meier curve with the y axis denoting the % remaining non-diabetic mice. Statistical analysis was performed using log rank (Prism 4.0).

Figure 6:
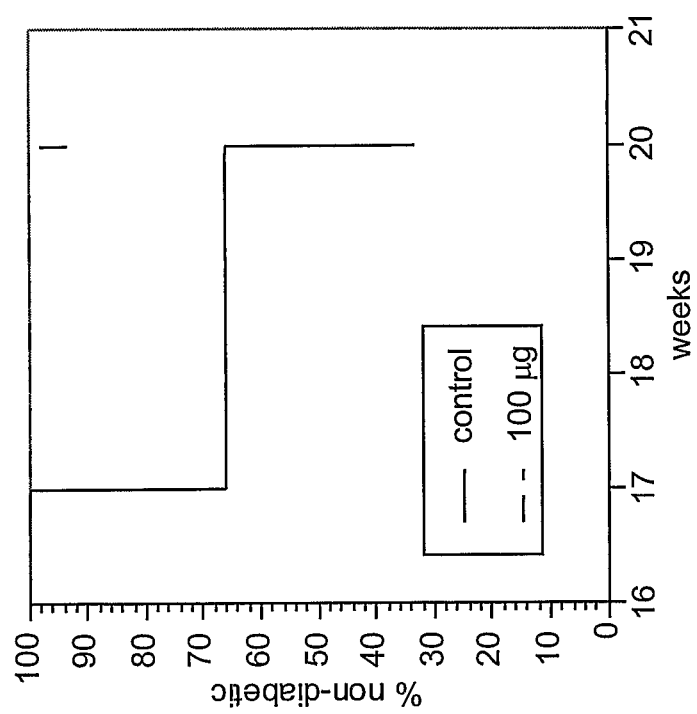
FIG. 6 Mice were fed 100 μg SIRS (n=10) (dashed line) or mock treated (n=12) (solid line), and the percent of mice that became diabetic was plotted starting at 18 weeks.
Figure 7:
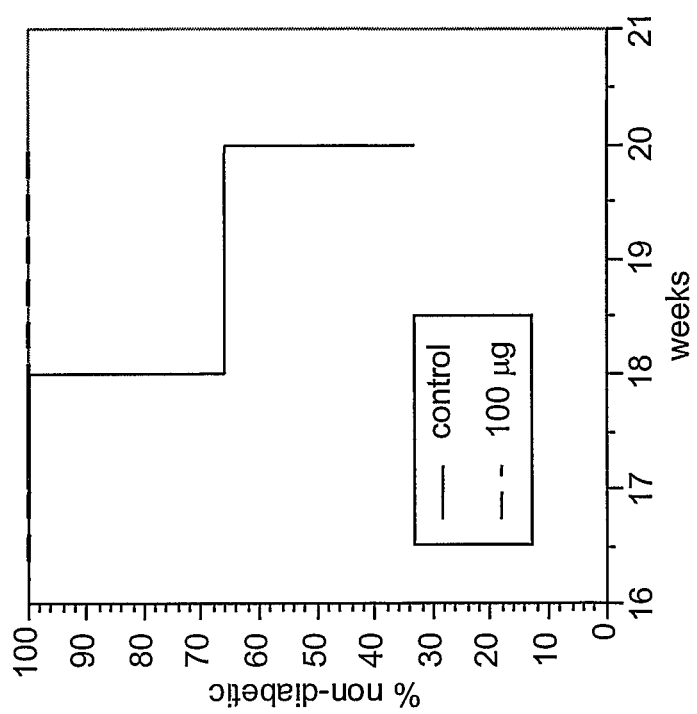
FIG. 7 Mice were fed 100 μg SIRS (n=8) (dashed line) or mock treated (n=8) (solid line), and the percent of mice that became diabetic was plotted starting at 18 weeks.

Every day ingestion of SIRS peptide from age ten weeks to 20 weeks inhibit diabetes mellitus in NOD mice. Mice fed 100 μg SIRS demonstrated significantly delayed onset of T1DM and decreased frequency of mice becoming diabetic compared to mock treated mice (FIG. 6 and FIG. 7).

REFERENCES

The following references, to the extent that they provide exemplary procedural or other details supplementary to those set forth herein, are specifically incorporated herein by reference.

U.S. Pat. No. 4,554,101
U.S. Patent Application 20040151694
Alvord, E. C. et al., *Ann. NY Acad. Sci.* 122:333, 1965.
Aune, T. M. et al., *J. Immunol.* 127:368, 1981.
Aune, T. M. et al., *J. Immunol. Methods* 53:1, 1982.
Aune, T. M. et al., *J. Immunol.* 135:2768, 1985.
Bangham et al., *J. Mol. Biol.*, 13(1):253-259, 1965.
Deamer and Uster, In: Liposome Preparation: Methods and Mechanisms, Ostro (Ed.), Liposomes, 1983.
Devens, B. H. et al., *J. Immunol.* 138:3688, 1987.
Gregoriadis, In: *Drug Carriers in Biology and Medicine*, Gregoriadis (Ed.), 287-341, 1979.
Krakauer, R. S. Et al., *Science* 196:56, 1977.
Kyte and Doolittle, *J. Mol. Biol.*, 157:105-132, 1982.
Lublin, F., *Ann. Neurol.* 17:188, 1985.
Jones, R. R. et al., *J Neuroimmunol.* 57:155, 1995.
Peters, B. A. et al., *Cell Immunol.* 69:75, 1982.
Remington's Pharmaceutical Sciences, 18th Ed. Mack Printing Company, pp. 1289-1329, 1990.
Schnaper, H. W. et al., *J. Immunol.* 131:2301, 1983.
Schnaper, H. W. et al., *J. Immunol.* 132:2429, 1984.
Schnaper, H. W. et al., *J. Clin. Invest.* 76:341, 1985.
Schnaper, H. W. et al., *Cell Immunol.* 141:3148, 1988.
Szoka and Papahadjopoulos, *Proc. Natl. Acad. Sci. USA*, 75:4194-4198, 1978.
Tadakuma, T. et al., *J. Immunol.* 117:323, 1976.
Tadakuma, T. et al., *J. Immunol.* 117:967, 1976.
Webb, D. R. et al., *J. Immunol.* 135:3238, 1985.
Webb, D. R., et al., *Int. Immunol.* 2:765, 1990.
Zimecki, M. et al., *Immunopharmacology* 19:39, 1990.

The invention claimed is:

1. A method of immunotherapy in an individual comprising orally administering to the individual a therapeutically effective amount of a SIRS polypeptide comprising the N-terminal amino acid sequence (SEQ ID NO:5):

X1-X2-X3-X3-X4-X4-X4-X4-X4-X4-Pro-X5-X2-X2-X6-X4-X4-X7-X7-X3-X4 wherein X1 is Met, Val, Leu or Cys;
X2 is Thr, Ala or Gly;
X3 is Glu, Arg, Asp or Lys;
X4 is Gln, Ser, Asn or Gly;
X5 is Glu, Arg, Asp or Lys;
X6 is Ile, Leu, Val, Met or Thr, and;
X7 is Ala, Cys, Thr or Gly, and
wherein said polypeptide is not SIRS-a7, SIRS-a6 or SIRS-a5.

2. The method of claim 1, wherein X1 is Met, Leu or Cys.
3. The method of claim 1, wherein X2 is Thr or Gly.
4. The method of claim 1, wherein X3 is Glu, Asp or Lys.
5. The method of claim 1, wherein X4 is Gln, Ser, or Asn.
6. The method of claim 1, wherein X5 is Arg, Asp or Lys.
7. The method of claim 1, wherein X6 is Ile, Leu, Val, or Thr.
8. The method of claim 1, wherein X7 is Ala, Thr or Gly.
9. The method of claim 1, wherein X3 is Asp or Glu.
10. The method of claim 6, wherein X5 is Lys or Arg.
11. The method of claim 1, wherein the polypeptide comprises the sequence of SEQ ID NO:1.
12. The method of claim 11, wherein the polypeptide is SEQ ID NO:1.
13. The method of claim 2, wherein X1 is Met.
14. The method of claim 1, wherein the immunotherapy is for the treatment of an autoimmune disease.
15. The method of claim 14, wherein said autoimmune disease is rheumatoid arthritis, psoriasis, type 1 diabetes, SLE, transplant rejection, autoimmune thyroid disease (Hashimoto's disease), sarcoidosis, scleroderma, granulomatous vasculitis, Crohn's disease, ulcerative colitis, Sjögren's disease, ankylosing spondylitis, polymyositis dermatomyositis, polyarteritis nodosa, immunologically mediated blistering skin diseases, Behçet's syndrome, multiple sclerosis, systemic sclerosis, Goodpasture's disease or immune mediated glomerulonephritis.
16. The method of claim 15, wherein said autoimmune disease is multiple sclerosis.
17. The method of claim 15, wherein the autoimmune disease is type 1 diabetes.
18. The method of claim 1, wherein said individual is a human.
19. The method of claim 14, wherein the immunotherapy reduces the severity of said autoimmune disease.
20. The method of claim 14, wherein the immunotherapy delays the onset of said autoimmune disease.
21. The method of claim 1, wherein the polypeptide is formulated in a caplet.
22. The method of claim 1, further comprising administering an interferon alpha.
23. The method of claim 1, further comprising administering a steroid.
24. A method for treating or preventing Type 1 diabetes or multiple sclerosis in an individual comprising administering to the individual a therapeutically effective amount of a SIRS polypeptide comprising the N-terminal amino acid sequence (SEQ ID NO:5):

X1-X2-X3-X3-X4-X4-X4-X4-X4-X4-Pro-X5-X2-X2-X6-X4-X4-X7-X7-X3-X4 wherein X1 is Met, Val, Leu or Cys;
X2 is Thr, Ala or Gly;
X3 is Glu, Arg, Asp or Lys;
X4 is Gln, Ser, Asn or Gly;
X5 is Glu, Arg, Asp or Lys;
X6 is Ile, Leu, Val, Met or Thr, and;
X7 is Ala, Cys, Thr or Gly, and
wherein said polypeptide is not SIRS-a7, SIRS-a6 or SIRS-a5.

25. The method of claim 24, wherein X1 is Met, Leu or Cys.
26. The method of claim 24, wherein X2 is Thr or Gly.
27. The method of claim 24, wherein X3 is Glu, Asp or Lys.
28. The method of claim 24, wherein X4 is Gln, Ser, or Asn.
29. The method of claim 24, wherein X5 is Arg, Asp or Lys.
30. The method of claim 24, wherein X6 is Ile, Leu, Val, or Thr.
31. The method of claim 24, wherein X7 is Ala, Thr or Gly.
32. The method of claim 24, wherein X3 is Asp or Glu.
33. The method of claim 29, wherein X5 is Lys or Arg.
34. The method of claim 24, wherein the polypeptide comprises the sequence of SEQ ID NO:1.
35. The method of claim 24, wherein the polypeptide is SEQ ID NO:1.
36. The method of claim 24, wherein X1 is Met.
37. The method of claim 24, further defined as a method for treating or preventing multiple sclerosis.
38. The method of claim 24, further defined as a method for treating or preventing type 1 diabetes.
39. The method of claim 24, wherein said composition is administered orally or subcutaneously.
40. The method of claim 24, wherein said individual is a human.
41. The method of claim 37, further defined as a method for reducing the severity of multiple sclerosis symptoms.
42. The method of claim 38, further defined as a method for reducing the severity of type 1 diabetes.
43. The method of claim 38, further defined as a method for delaying the onset of type 1 diabetes.
44. The method of claim 24, wherein the polypeptide is formulated in a caplet.
45. The method of claim 24, further comprising administering an interferon alpha.
46. The method of claim 24, further comprising administering a steroid.
47. The method of claim 1, wherein the polypeptide is a synthetic polypeptide.
48. The method of claim 24, wherein the polypeptide is a synthetic polypeptide.

* * * * *

SEQUENCE LISTING

```
<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
```

```
<223> OTHER INFORMATION: Synthetic peptide

<400> SEQUENCE: 1

Met Thr Glu Glu Asn Gln Gln Ser Ser Gln Pro Lys Thr Thr Ile Asn
1               5                   10                  15

Asn Ala Gly Asp Ser
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Met Glu Val Gly Trp Tyr Arg Ser Pro Phe Ser Arg Val Val His Leu
1               5                   10                  15

Tyr Arg Asn Gly Lys
            20

<210> SEQ ID NO 3
<211> LENGTH: 66
<212> TYPE: DNA
<213> ORGANISM: Artificial Sequence
<220> FEATURE:
<223> OTHER INFORMATION: Synthetic primer

<400> SEQUENCE: 3
atgaccgagg agaaccagca gagcagccag cctaagacca ccatcaacaa cgccggcaac      60
agctga                                                                66

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(21)
<223> OTHER INFORMATION: Xaa can be any naturally occurring amino acid

<400> SEQUENCE: 4

Xaa Xaa Xaa Xaa Xaa Xaa Xaa Xaa Xaa Xaa Pro Xaa Xaa Xaa Xaa Xaa
1               5                   10                  15

Xaa Xaa Xaa Xaa Xaa
            20

<210> SEQ ID NO 5
<211> LENGTH: 66
<212> TYPE: DNA
<213> ORGANISM: Artificial Sequence
<220> FEATURE:
<223> OTHER INFORMATION: Synthetic primer

<400> SEQUENCE: 5
atgaccgaag aaaatcagca gagcagccag ccgaaaacca ccattaataa tgcgggcaat      60
agctaa                                                                66
```